US012768916B2

(12) United States Patent
Kotecha et al.

(10) Patent No.: US 12,768,916 B2
(45) Date of Patent: Oct. 20, 2026

(54) COMPOSITE SPIN PROBES WITH SELECTABLE OXYGEN SENSITIVITY FOR ELECTRON PARAMAGNETIC RESONANCE

(71) Applicant: O2M Technologies, LLC, Chicago, IL (US)

(72) Inventors: Mrignayani Kotecha, Chicago, IL (US); Navin Viswakarma, La Grange Park, IL (US)

(73) Assignee: O2M Technologies, LLC, Chicago, IL (US)

( * ) Notice: Subject to any disclaimer, the term of this patent is extended or adjusted under 35 U.S.C. 154(b) by 152 days.

(21) Appl. No.: 18/968,554

(22) Filed: Dec. 4, 2024

(65) Prior Publication Data

US 2025/0180679 A1 Jun. 5, 2025

Related U.S. Application Data

(60) Provisional application No. 63/606,322, filed on Dec. 5, 2023.

(51) Int. Cl.
*G01V 3/00* (2006.01)
*A61K 49/20* (2006.01)
(Continued)

(52) U.S. Cl.
CPC ............ *G01R 33/285* (2013.01); *A61K 49/20* (2013.01); *G01R 33/60* (2013.01); *A61B 5/055* (2013.01)

(58) Field of Classification Search
CPC ...... G01R 33/285; G01R 33/60; A61K 49/20; A61B 5/055
(Continued)

(56) References Cited

U.S. PATENT DOCUMENTS 4,537,661 A * 8/1985 Lee ...................... G01N 33/005 205/794.5

FOREIGN PATENT DOCUMENTS

| | | | | | |
|---|---|---|---|---|---|
| CN | 101446540 | A | * | 6/2009 | |
| CN | 110857311 | A | * | 3/2020 | .............. A61P 35/00 |
| WO | WO-2008096280 | A1 | * | 8/2008 | ........... A61K 49/186 |

OTHER PUBLICATIONS

Ahmad, et al., "Theory, Instrumentation, and Applications of EPR Oximetry", "Chem Rev.", May 12, 2010, pp. 3212-3236, vol. 110, No. 5.

(Continued)

*Primary Examiner* — Walter L Lindsay, Jr.
*Assistant Examiner* — Frederick Wenderoth
(74) *Attorney, Agent, or Firm* — Charles A. Lemaire; Lemaire Patent Law Firm, P.L.L.C.

(57) ABSTRACT

A novel class of particulate probes for electron paramagnetic resonance (EPR) oximetry with adjustable relaxation rates sensitivity to oxygen partial pressure is described. The probe includes oxygen-sensitive paramagnetic spin probes such as lithium phthalocyanine (LiPc) mixed with non-paramagnetic additives such as bonewax, beeswax, or petroleum jelly. The sensitivity of the probe's relaxation rate constants to oxygen can be controlled through the selection of additives and mixing ratios. The probe exhibits reduced oxygen sensitivity and expanded dynamic range compared to an unmodified probe, enabling pulse EPR measurements across the full physiological oxygen range (0-160 torr) and full oxygen dynamic range (0-760 torr). The probe can be shaped as needed for tissue implantation and serve as multimodal imaging markers for EPR and other imaging modalities.

29 Claims, 12 Drawing Sheets

(51) Int. Cl.
*G01R 33/28* (2006.01)
*G01R 33/60* (2006.01)
*A61B 5/055* (2006.01)

(58) Field of Classification Search
USPC .......................................................... 324/318
See application file for complete search history.

(56) References Cited

OTHER PUBLICATIONS

Epel, et al., "How in vivo EPR measures and images oxygen", "In: H.M. Swartz et al. (eds.), Oxygen Transport to Tissue XXXVI, Advances in Experimental Medicine and Biology", 2014, pp. 113-119.

Liu, et al., "Lithium phthalocyanine: A probe for electron paramagnetic resonance oximetry in viable biological systems", "Proc. Natl. Acad. Sci.—Biophysics", Jun. 1993, pp. 5438-5442, vol. 90.

Meenakshisundaram, et al., "Oxygen sensitivity and biocompatibility of an implantable paramagnetic probe for repeated measurements of tissue oxygenation", "Biomed Microdevice", Aug. 2009, pp. 817-826, vol. 11, No. 4.

Swartz, "History of EPR Studies from the H. M. Swartz Laboratories: Part 3—EPR Oximetry", "Applied Magnetic Resonance", Jan. 11, 2022.

* cited by examiner

Mouse euthanized on day 24
FIG. 6C
FIG. 6D
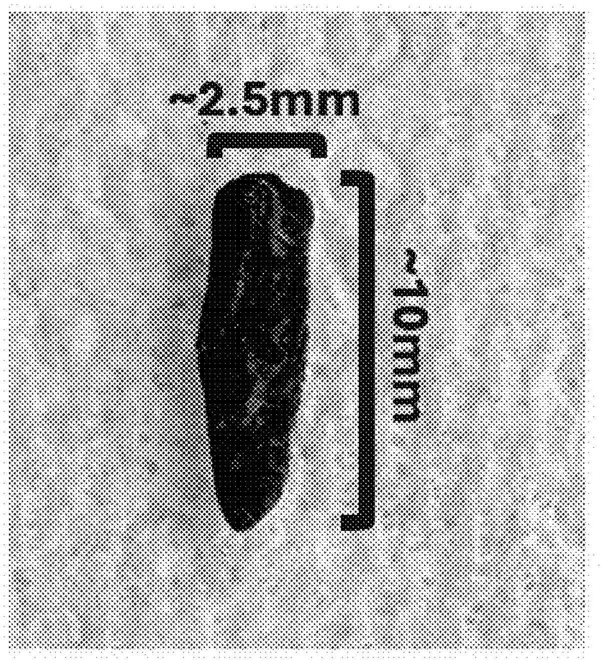

COMPOSITE SPIN PROBES WITH SELECTABLE OXYGEN SENSITIVITY FOR ELECTRON PARAMAGNETIC RESONANCE

CLAIM OF PRIORITY

This patent application claims the benefit of priority of U.S. Provisional Patent Application Ser. No. 63/606,322, filed on Dec. 5, 2023, which is hereby incorporated by reference herein in its entirety.

TECHNICAL FIELD

This document pertains generally, but not by way of limitation, to electron paramagnetic resonance spectroscopy and electron paramagnetic resonance imaging.

BACKGROUND

Electron paramagnetic resonance (EPR), also known as electron spin resonance (ESR), is a magnetic resonance technique where paramagnetic species like radicals are exposed to a constant magnetic field to produce EPR signals when excited by radiofrequency radiation (John A. Weil, James R. Bolton 2007, ISBN: 978-0-470-08497-7).

A specialized variant called pulse EPR (pEPR) employs radiofrequency pulses of alternating magnetic field (B1) to manipulate electron spin magnetization. EPR relaxometry studies the relaxation dynamics of paramagnetic species through spin-spin relaxation time ($T_2$) and spin-lattice relaxation time ($T_1$). These parameters reflect interactions between paramagnetic species and their environment.

One application of EPR relaxometry is oximetry—the measurement of oxygen concentrations through EPR spectroscopy and imaging (Epel and Halpern, 2015 DOI: 10.1039/9781849734837-00180; Epel et al 2014 PMID: 24729222, DOI: 10.1007/978-1-4939-0620-8_15; Ahmad and Kuppusamy 2010, PMID: 20218670 DOI: 10.1021/cr900396q). The oxygen partial pressure ($pO_2$) affects the relaxation rates ($R_1=1/T_1$ and $R_2=1/T_2$) and line broadening of paramagnetic species, enabling oxygen measurements in biological systems, including live cells, tissues, animals, and humans.

Two classes of EPR-sensitive probes are used for oximetry (Epel and Halpern 2015, DOI: 10.1039/9781849734837-00180, Smirnova et al. 2009, https://doi.org/10.1002/9780470027318.a9049). A first probe class includes solid probes (crystalline or particulate), which can be embedded in tissues for longitudinal measurements. A second probe class includes soluble probes, which allow for noninvasive three dimensional imaging but require repeated injections for each measurement.

The oxygen effect on these probes follows Heisenberg exchange principles, where oxygen quenches radiofrequency-induced excitation at a relaxation rate, $R_1$ or $R_2$, proportional to oxygen concentration. While higher sensitivity enables more precise measurements, it limits the measurable oxygen range. Conversely, lower sensitivity allows measurement across wider oxygen ranges (0-760 mmHg) but with reduced precision (Gunnar and Schweiger 2001, ISBN-13.978-0198506348). pEPR is capable of highly precise determination of relaxation times, however, signals with too short relaxation times may be beyond its detection capabilities. Therefore, pEPR can be applied only to specific spin probes and specific ranges of oxygen concentrations in which signals are detected.

Some particulate/crystalline probes include derivatives of alkali metal phthalocyanines (Liu et al. 1993 PMID: 8390665; Pandian, et al. 2003 PMID: 14572616; Frank et al., 2015, PMID: 26459034). Examples can include lithium phthalocyanine (LiPc), lithium naphthalocyanine (LiNc), and lithium octa-n-butoxynaphthalocyanine (LiNc-BuO). LiNc-BuO can further have small alterations in oxygen sensitivity based on their crystal size, and those are depicted as low sensitivity LiNc-BuO (LiNc-BuO-LS) and higher sensitivity LiNc-BuO (LiNc-BuO-HS). LiPc and LiNc-BuO are crystals, but when they are in powder form, they are also called particulates.

These crystalline materials form molecular stacks with strongly coupled electronic structures and gas-accessible channels (Pandiuan et al. 2009, PMID: 19809598). The resulting radicals produce strong, single exchange-narrowed EPR signals.

While LiPc and LiNc-BuO probes can be used for EPR oximetry measurements in biological systems (Epel and Halpern 2015 DOI: 10.1039/9781849734837-00180, Swartz https://doi.org/10.1007/s00723-021-01454-8), they have limitations. These probes are typically embedded in materials like Polydimethylsiloxane (PDMS) for environmental protection, though this does not alter their oxygen sensitivity in a meaningful way (Meenakshisundaram et al Biomedical Microdevices 2009 PMID 19319683 DOI: 10.1007/s10544-009-9298-4). Some applications use continuous-wave EPR detection (Illangovan et al, Journal of Magnetic Resonance, 2004, DOI: 10.1016/j.jmr.2004.05.018), with limited use in pulse EPR (Viswakarma et al. 2022, PMID 35509263) due to these probes' high oxygen sensitivity restricting measurements to low oxygen concentrations (0-60 torr).

There remains a critical need for particulate probes compatible with pulse EPR techniques across the full range of physiological (0-160 torr, or 21% $O_2$) and dynamic oxygen concentrations (0-760 torr, or 100% $O_2$) to enable advanced applications in oxygen spectroscopy and imaging.

SUMMARY

This document describes novel composite probes for electron paramagnetic resonance (EPR) oximetry with selectable sensitivity to oxygen partial pressure.

A composite probe can be created by combining paramagnetic particulate or crystalline spin probes with non-paramagnetic additives to achieve specific oxygen sensing properties.

A composite probe can include oxygen-sensitive paramagnetic spin probes such as lithium phthalocyanine (LiPc) or lithium naphthalocyanine (LiNc-BuO). This can be combined with various waxy additive materials such as bone-wax, beeswax, and petroleum jelly. Waxes are a diverse class of organic compounds that are lipophilic, malleable solids near ambient temperatures. They include higher alkanes and lipids, typically with melting points above about 40° C. (104° F.), melting to give low viscosity liquids. Waxes are insoluble in water but soluble in nonpolar organic solvents such as hexane, benzene and chloroform. Natural waxes of different types are produced by plants and animals and occur in petroleum. The additive material can also be petroleum-derived oily hydrocarbons. Petroleum oily hydrocarbons (PHCs) are a large group of chemicals that do not evaporate and don't burn very well. A specific oxygen sensitivity can be achieved through defined choices of additives and mixture ratios.

A composite probe offers several benefits, including precisely selectable sensitivity to oxygen partial pressure and an expanded measurement range for pulse EPR applications. In addition, a composite probe can be configured for oxygen measurements at elevated oxygen levels not possible with standard probes and can be configured as a marker for multiple imaging modalities.

This document demonstrates a relationship between oxygen partial pressure ($pO_2$) and relaxation rate constants ($R_1$ or $R_2$) for specific probe compositions. In addition, this document demonstrates in vivo functionality for tissue oxygen measurements under different breathing conditions and demonstrates application as fiducial markers in EPR imaging.

The development enables pulse EPR oximetry and imaging across the full range of oxygen concentrations, addressing a significant limitation of existing particulate probes.

Each of these non-limiting examples can stand on its own, or can be combined in various permutations or combinations with one or more of the other examples.

This overview is intended to provide an overview of the subject matter of the present patent application. It is not intended to provide an exclusive or exhaustive explanation of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 6C illustrates probe placement in an animal, according to one example.

FIG. 6D illustrates individual probe dimensions, according to one example.

DETAILED DESCRIPTION

Figure 1A:
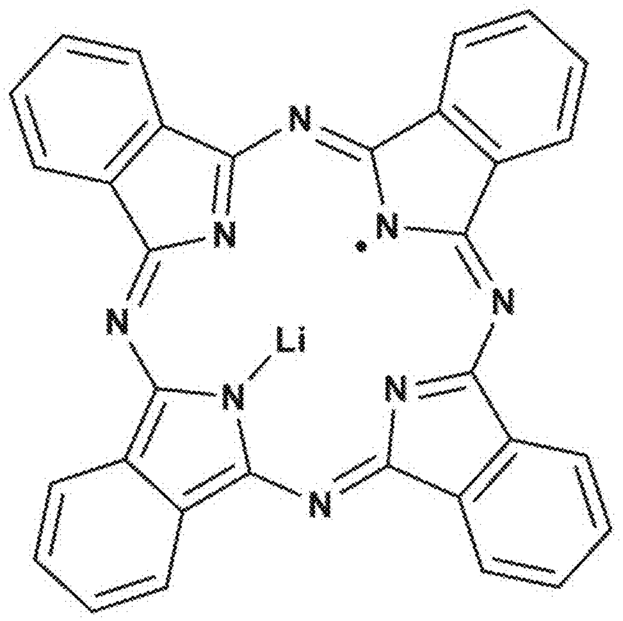
FIG. 1A illustrates the chemical structure of LiPc, according to one example.
Figure 1B:
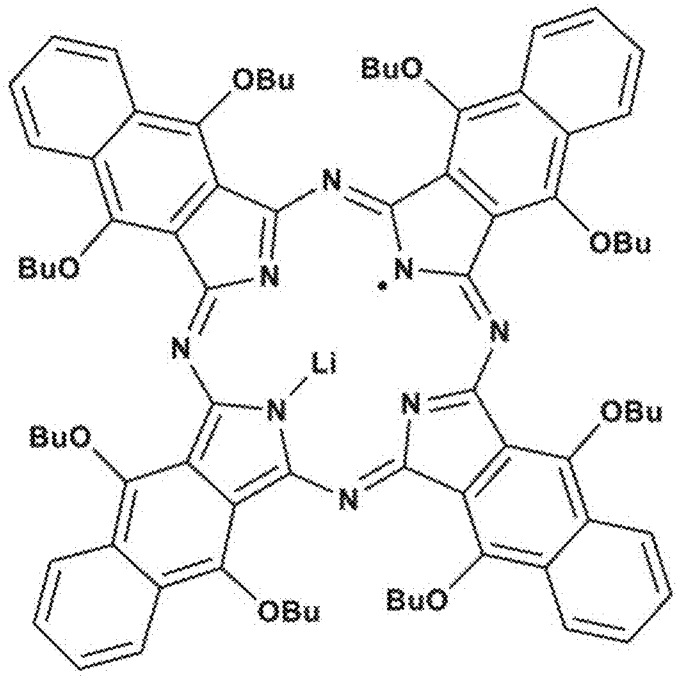
FIG. 1B illustrates the chemical structure of LiNc-BuO, according to one example.

FIGS. 1A and 1B provide detailed chemical structures of two primary particulate probes used in EPR oximetry.

FIG. 1A shows the chemical structure of Lithium phthalocyanine (LiPc), which includes:

a central lithium (Li) atom four pyrrole rings connected in a cyclic arrangement nitrogen atoms forming bridges between the pyrrole units a planar macrocyclic structure with conjugated double bonds FIG. 1B depicts the chemical structure of Lithium octa-n-butoxynaphthalocyanine (LiNc-BuO), which includes:

a central lithium (Li) atom an extended naphthalocyanine ring system eight butoxy (OBu) substituent groups symmetrically arranged around the periphery a larger conjugated system compared to LiPc the notation "BuO" representing butoxy groups attached at regular intervals around the molecule These structures represent the fundamental building blocks that form crystalline solids with stacked molecules, creating strongly coupled electronic structures and channels for gas access, which are exhibit oxygen sensing capabilities.

FIG. 2A and FIGS. 2B-2H provides a comprehensive illustration of the composite probe preparation process, specifically demonstrating the creation of a LiPc-BW5 probe, in which LiPc is mixed with bonewax in a 1:5 ratio.

Figure 2A:
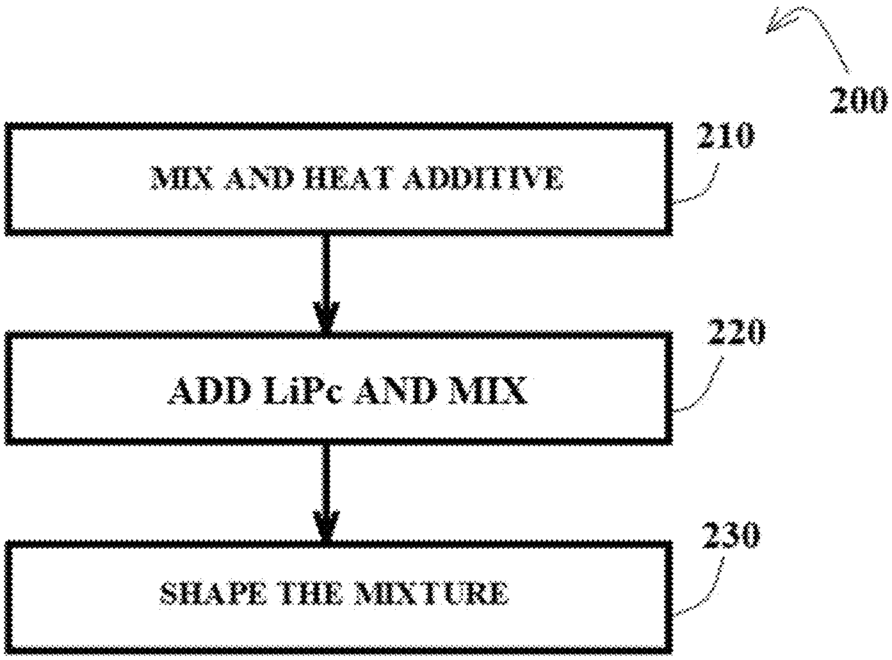
FIG. 2A illustrates a flow chart of a method for preparing a composite probe, according to one example.

FIG. 2A presents a flowchart of method 200 for preparing a composite probe for electron paramagnetic resonance measurements.

At 210, method 200 includes mixing and heating an additive. In one example, the additive is mixed in a glass petri dish and heated in a microwave oven. Mixing can include stirring with an implement such as a metal rod. The additive can include, for example, bonewax.

At 210, method 200 includes adding a measured quantity of a particulate paramagnetic probe crystal to the heated additive material. In one example, the particulate paramagnetic probe crystal includes LiPc. Method 200 includes mixing the additive and the paramagnetic probe crystal.

At 230, method 200 includes shaping the composite mixture. The mixture can be shaped by, in various examples, kneading into a pellet form, extruding, or molding into a tubular form or other shape for subsequent use.

In a specific example, the composite probe is prepared by:

placing 50 mg of bonewax in a glass petri dish;

mashing the bonewax using a steel rod;

heating the mashed bonewax in a microwave oven for 1 minute;

adding 10 mg of LiPc crystal to the heated bonewax;

mixing the LiPc crystal thoroughly with the heated bonewax using a steel rod to form a composite mixture in a 1:5 ratio; and rolling the composite mixture between fingers to shape it as needed for the intended application.

The resulting composite probe is a soft and versatile material that can be shaped into any desired form for further use.

Figure 2B:
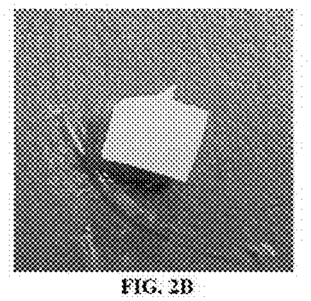
FIG. 2B-2H illustrates a sequence of images for preparing a composite probe, according to one example.
Figure 2C:
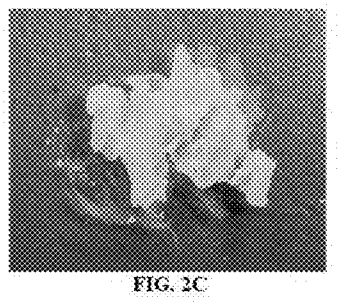
Figure 2D:
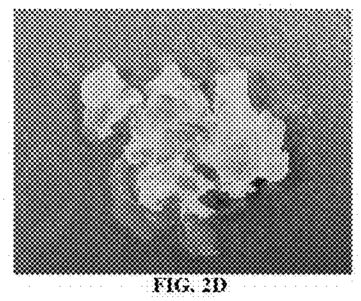
Figure 2E:
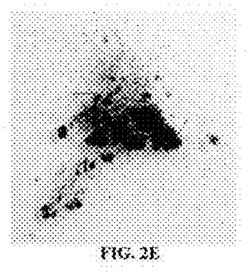
Figure 2F:
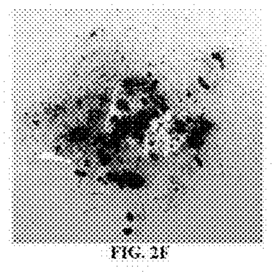
Figure 2G:
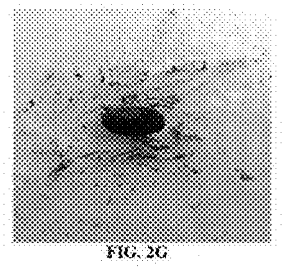
Figure 2H:
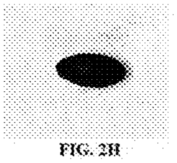

FIGS. 2B-2H shows sequential photographs illustrating a probe development process. For example, FIG. 2B depicts an initial preparation of 50 mg of bonewax in a glass petri dish. In FIG. 2C, the bonewax is mashed using a steel rod. In FIG. 2D, the bonewax is shown following heating in a microwave oven for one minute. FIG. 2E illustrates addition of 10 mg LiPc crystal and FIG. 2F illustrates mixing of 50 mg bonewax with 10 mg LiPc. FIG. 2G shows the composite probe following shaping by rolling or kneading between fingers. A completed probe is illustrated in FIG. 2H.

Table 1 (below) states $T_1$ values of electron spins at 37° C. at 25 mT magnetic field and at 720 MHz resonance frequency for 0% (0 torr), 21% $O_2$ (160 torr) for particulate probe alone, and with additive media. In one example, the $T_1$ value is also provided at 100% $O_2$ (760 torr).

TABLE 1

| Probe | Additive Media | Quantity | 0% $O_2$ Mean ± STD (μs) | 21% $O_2$ Mean ± STD (μs) | 100% $O_2$ Mean ± STD (μs) |
|---|---|---|---|---|---|
| — | Bonewax | 50 mg | No Signal | No Signal | |
| LiPc | — | 10 mg | 3.999 ± 0.001 | No Signal | |
| LiPc | PDMS | 1:5 | 3.781 ± 0.001 | No Signal | |
| LiPc | Bonewsx | 1:5 | 4.169 ± 0.001 | 1.492 ± 0.001 | 0.469 ± 0.002 |
| LiPc | Bonewax | 1:20 | 5.481 ± 0.001 | 1.969 ± 0.002 | |
| LiPc | Petroleum Jelly | 1:5 | 4.982 ± 0.013 | 1.269 ± 0.005 | |
| LiPc | Beeswax | 3:5 | 4.860 ± 0.002 | 1.395 ± 0.010 | |
| LiNc-BuO-LS | — | 10 mg | 1.357 ± 0.001 | No Signal | |
| LiNc-BuO-LS | PDMS | 1:5 | 1.440 ± $7e^{-4}$ | No Signal | |
| LiNc-BuQ-LS | Bonewax | 1:5 | 1.496 ± $4e^{-4}$ | No Signal | |
| LiNc-BuO-LS | Bonewax | 1:20 | 1.366 ± 0.001 | No Signal | |
| LiNc-BuO-HS | — | 10 mg | 1.347 ± $5e^{-4}$ | No Signal | |
| LiNc-BUO-HS | PDMS | 1:5 | 1.309 ± $3e^{-4}$ | No Signal | |
| LiNc-BUO-AS | Bonewax | 1:5 | 1.336 ± $3e^{-4}$ | No Signal | |
| LiNc-BuO-HS | Bonewax | 1:20 | 0.934 ± $6e^{-4}$ | No Signal | |

Table 2 (below) states $T_2$ values of electron spins at 37° C. at 25 mT magnetic field and at 720 MHz resonance frequency for 0% (0 torr), 21% $O_2$ (160 torr) for particulate probe alone, and with additive media. In one example, the $T_1$ value is also provided at 100% $O_2$ (760 torr).

TABLE 2

| Probe | Additive Media | Quantity | 0% $O_2$ Mean ± STD (μs) | 21% $O_2$ Mean ± STD (μs) | 100% $O_2$ Mean ± STD (μs) |
|---|---|---|---|---|---|
| — | Bonewax | 50 mg | No Signal | No Signal | |
| LiPc | — | 10 mg | 3.329 ± 0.001 | No Signal | |
| LiPc | PDMS | 1:5 | 3.563 ± 0.001 | No Signal | |
| LiPc | Bonewax | 1:5 | 3.494 ± 0.004 | 1.435 ± 0.001 | 0.536 ± 0.004 |
| LiPc | Bonewax | 1:20 | 4.973 ± 0.003 | 2.048 ± 0.004 | |
| LiPc | Petroleum Jelly | 1:5 | 4.520 ± 0.011 | 1.291 ± 0.002 | |
| LiPc | Beeswax | 1:5 | 4.040 ± 0.007 | 1.243 ± 0.002 | |
| LiNc-BuO-LS | — | 10 mg | 1.364 ± 0.001 | No Signal | |
| LiNc-BUO-LS | PDMS | 1:5 | 1.482 ± 0.001 | No Signal | |
| LiNc-BUO-LS | Bonewsx | 1:5 | 1.506 ± 0.001 | No Signal | |
| LiNc-BuO-LS | Bonewax | 1:20 | 1.451 ± 0.002 | No Signal | |
| LiNc-BuO-HS | — | 10 mg | 1.314 ± $3e^{-4}$ | No Signal | |
| LiNc-BuO-HS | PDMS | 1:5 | 1.209 ± $9e^{-4}$ | No Signal | |
| LiNc-BuO-AS | Bonewax | 1:5 | 1.417 ± $9e^{-4}$ | No Signal | |
| LiNc-BuO-HS | Bonewax | 1:20 | 1.098 ± $7e^{-4}$ | No Signal | |

Figure 3A:
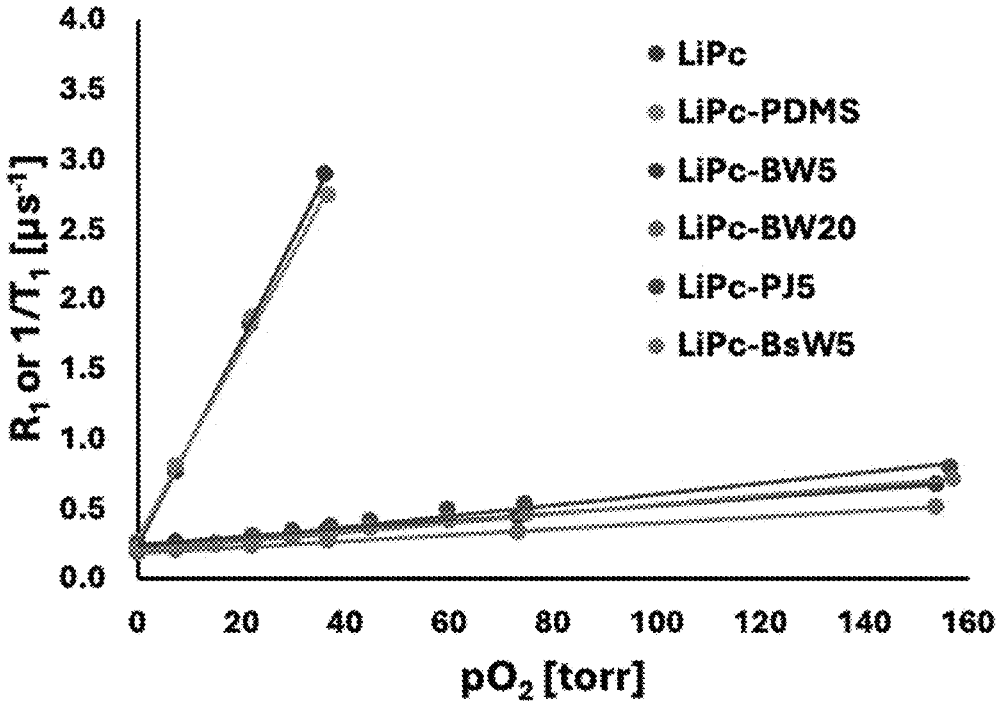
FIG. 3A illustrates a relationship between $R_1$ relaxation and oxygen concentration ($pO_2$) for various LiPc-based materials, according to one example.
Figure 3B:
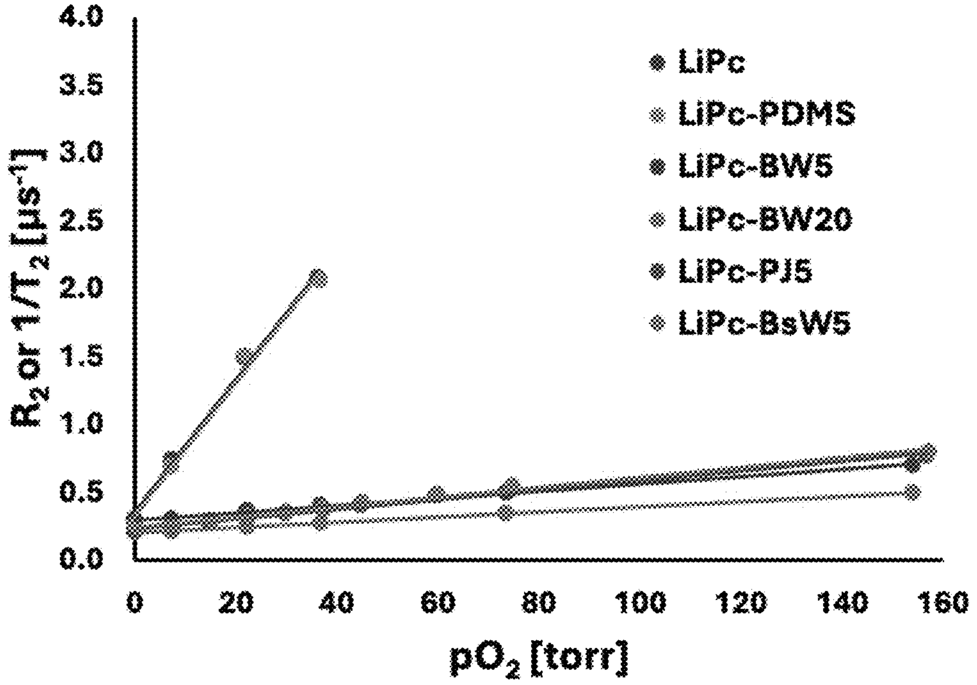
FIG. 3B illustrates a relationship between $R_2$ relaxation and oxygen concentration ($pO_2$) for various LiPc-based materials, according to one example.

FIGS. 3A and 3B illustrate relationships between relaxation rates and oxygen concentration for various LiPc-based materials. FIGS. 3A and 3B demonstrate how embedding LiPc in different ratios of bonewax and other materials modifies the probe's oxygen sensitivity characteristics compared to the unmodified crystals and PDMS-embedded versions.

FIG. 3A shows $R_1$ ($=1/T_1$) relaxation rate as a function of oxygen concentration ($pO_2$). As shown, the display includes data points for multiple probe compositions including LiPc, LiPc-PDMS, LiPc-BW5, LiPc-BW20, LiPc-PJ5, and LiPc-BsW5. The figure demonstrates $R_1$ values ranging from 0 to approximately 3.5 $\mu s^{-1}$ and shows linear relationships between $R_1$ and $pO_2$ for each probe composition. The figure illustrates how composite materials exhibit reduced sensitivity compared to unmodified LiPc and documents a reduction in $R_1$ sensitivity between 1.1-34 times for composite probes.

FIG. 3B show $R_2$ ($=1/T_2$) relaxation rate as a function of oxygen concentration ($pO_2$). As shown, the figure illustrates parallel data for the same probe compositions. This demonstrates $R_2$ values ranging from 0 to approximately 2.5 $\mu s^{-1}$ and shows linear relationships between $R_2$ and $pO_2$ for each composition. The figure illustrates an expanded measurement range for composite materials compared to standard LiPc and LiPc-PDMS and documents reduction in $R_2$ sensitivity between 1-26 times for composite probes.

Table 3 (below) states the slope for $R_1$ and $R_2$ with $pO_2$ linear fit for LiPc, LiPc-PDMS, LiPc-BW5, LiPc-BW20, LiPc-PJ5, LiPc-PJ20, LiPc-BsW5 obtained from FIGS. 3A and 3B. The change in $R_1$ oxygen sensitivity of these materials compared to LiPc alone is LiPc: 1, LiPc-PDMS: 1.1, LiPc-BW5: 25.6, LiPc-BW20: 33.86, LiPc-PJ5-18.4, LiPc-BsW5: 21.71. The change in $R_2$ oxygen sensitivity of these materials compared to LiPc alone is LiPc: 1, LiPc-PDMS: 1, LiPc-BW5: 18.75, LiPc-BW20: 26.35, LiPc-PJ5-14, LiPc-BsW5: 13.8.

TABLE 3

| Probe | $R_1$ or $1/T_1$(Stope) | $R_2$ or $1/T_2$ (Slope) |
|---|---|---|
| LiPc | 14 | 20 |
| LiPc-PDMS | 15 | 20 |
| LiPc-BW5 | 359 | 375 |
| LiPc-BW | 474 | 527 |
| LiPc-PJ5 | 258 | 280 |
| LiPc-BsW5 | 304 | 276 |

Both FIGS. 3A, 3B and Table 3 demonstrate that all composite materials (LiPc-BW5, LiPc-BW20, LiPc-PJ5, LiPc-Bs-W5) exhibit an expanded range of measurement with oxygen concentrations compared to LiPc alone or LiPc embedded in PDMS, confirming reduced oxygen sensitivity and expanded dynamic range for EPR oximetry.

These materials represent different probe compositions, some examples of which include:

LiPc: Unaltered/pure lithium phthalocyanine crystals

LiPc-PDMS: Lithium phthalocyanine embedded in Polydimethylsiloxane (PDMS), which shields the probe from environmental factors other than oxygen without changing its oxygen sensitivity LiPc-BW5: Lithium phthalocyanine embedded in bonewax in a 1:5 ratio (10 mg LiPc to 50 mg bonewax), representing a composite probe with reduced oxygen sensitivity LiPc-BW20: Lithium phthalocyanine embedded in bonewax in a 1:20 ratio, showing further reduced oxygen sensitivity compared to LiPc-BW5

LiPc-PJ5: Lithium phthalocyanine embedded in petroleum jelly in a 1:5 ratio, providing another composite probe option with modified oxygen sensitivity LiPc-PJ20: Lithium phthalocyanine embedded in petroleum jelly in a 1:20 ratio, offering a more reduced oxygen sensitivity compared to LiPc-PJ5

LiPc-BsW5: Lithium phthalocyanine embedded in Beeswax in a 1:5 ratio, offering an alternative composite probe composition with distinct oxygen sensitivity characteristics FIG. 4A and FIG. 4B illustrate the relationship between relaxation rates and oxygen concentration for LiNc-BuO-LS (low oxygen sensitivity) based materials.

Figure 4A:
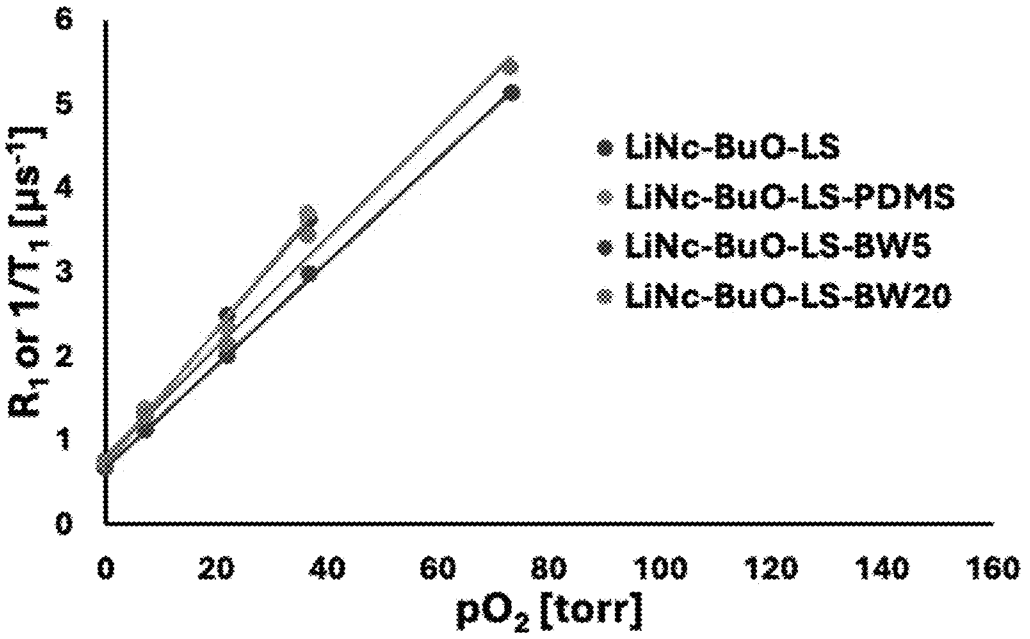
FIG. 4A illustrates a relationship between $R_1$ relaxation rates and $pO_2$ for LiNc-BuO-based samples, according to some examples.

FIG. 4A shows $R_1$ ($=1/T_1$) relaxation rate versus oxygen concentration ($pO_2$) and illustrates data for four compositions: LiNc-BuO-LS (unmodified crystals), LiNc-BuO-LS+PDMS (embedded in PDMS), LiNc-BuO-LS+BW (1:5) (low oxygen sensitivity LiNc-BuO embedded in bonewax 1:5 ratio), and LiNc-BuO-LS+BW (1:20) (LiNc-BuO-LS embedded in bonewax 1:20 ratio). The data demonstrates $R_1$ values ranging from 0 to approximately 6 $\mu s^{-1}$ and shows linear relationships between $R_1$ and $pO_2$ for each probe composition. The figure illustrates how bonewax composites exhibit different sensitivities compared to unmodified LiNc-BuO-LS.

Figure 4B:
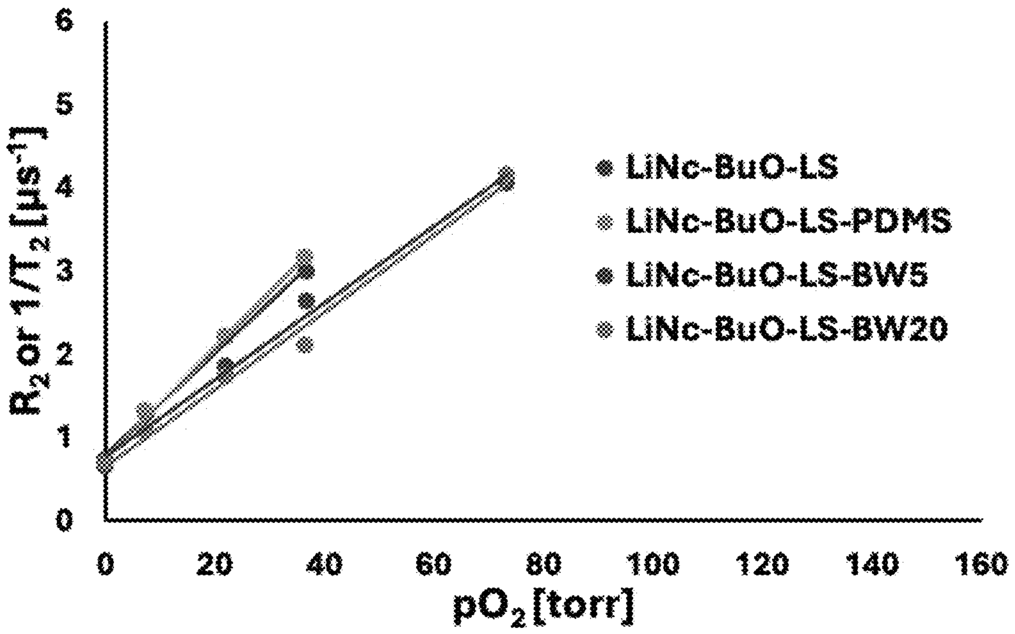
FIG. 4B illustrates a relationship between $R_2$ relaxation rates and $pO_2$ for LiNc-BuO-based samples, according to some examples.

FIG. 4B shows $R_2$ ($=1/T_2$) relaxation rate versus oxygen concentration ($pO_2$) and illustrates parallel data for the same four probe compositions. The data demonstrates $R_2$ values ranging from 0 to approximately 5 $\mu s^{-1}$ and shows linear relationships between $R_2$ and $pO_2$ for each composition. The figure illustrates how different compositions affect the probe's sensitivity to oxygen and shows an expanded measurement range for composite materials compared to standard LiNc-BuO-LS.

FIGS. 4A and 4B demonstrate how embedding LiNc-BuO-LS in different ratios of bonewax modifies the probe's oxygen sensitivity characteristics compared to the unmodified crystals and PDMS-embedded versions.

Table 4 (below) states the slope for $R_1$ and $R_2$ with $pO_2$ linear fit for LiNc-BuO-LS, LiNc-BuO-LS-PDMS, LiNc-BuO-LS-BW5, LiNc-BuO-LS-BW20. The change in $R_1$ oxygen sensitivity of these materials compared to LiNc-BuO-LS alone is LiNc-BuO-LS: 1, LiNc-BuO-LS-PDMS: 1, LiNc-BuO-LS-BW5: 1.23, LiNc-BuO-LS-BW20: 1.15. The change in $R_2$ oxygen sensitivity of these materials compared to LiNc-BuO-LS alone is LiNc-BuO-LS: 1, LiNc-BuO-LS-PDMS: 0.94, LiNc-BuO-LS-BW5: 1.19, LiNc-BuO-LS-BW20: 1.63.

TABLE 4

| Probe | $R_1$ or $1/T_1$(Stope) | $R_2$ or $1/T_2$ (Slope) |
|---|---|---|
| LiNc-BuO-LS | 13 | 16 |
| LiNc-BuO-LS-PDMS | 13 | 15 |
| LiNc-BuO-LS-BW5 | 16 | 19 |
| LiNc-BuO-LS-BW-20 | 15 | 26 |

Figure 5A:
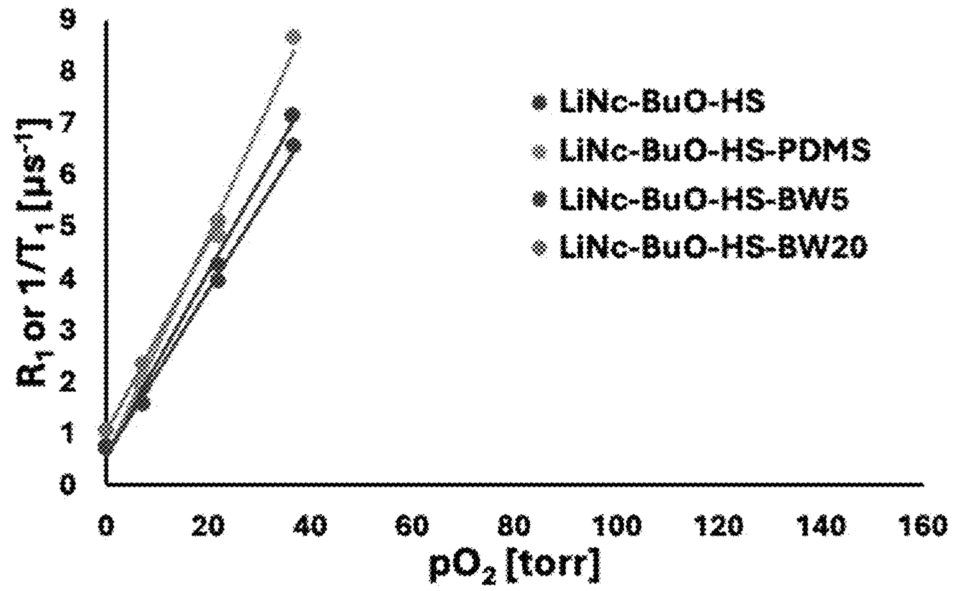
FIG. 5A illustrates a relationship between $R_1$ relaxation rates and $pO_2$ for LiNc-BuO-based samples, according to some examples.
Figure 5B:
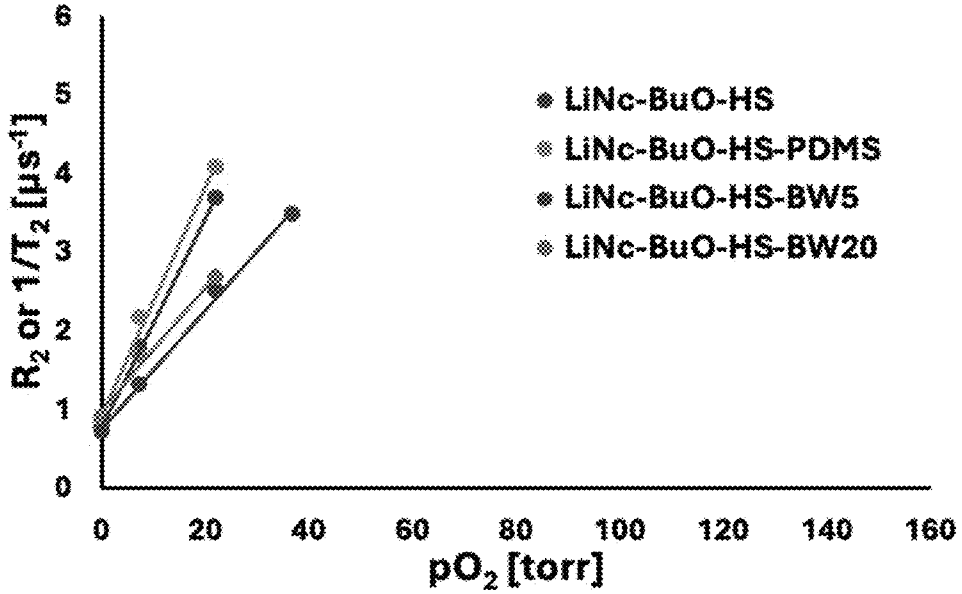
FIG. 5B illustrates a relationship between $R_2$ relaxation rates and $pO_2$ for LiNc-BuO-based samples, according to some examples.

FIG. 5A and FIG. 5B illustrate the relationship between relaxation rates and oxygen concentration for LiNc-BuO-HS (high oxygen sensitivity) based materials:

FIG. 5A shows $R_1$ ($=1/T_1$) relaxation rate versus oxygen concentration ($pO_2$) and illustrates data for four compositions: LiNc-BuO-HS (unmodified crystals), LiNc-BuO-HS+PDMS (embedded in PDMS), LiNc-BuO-HS+BW (1:5) (embedded in bonewax 1:5 ratio), and LiNc-BuO-HS+BW (1:20) (embedded in bonewax 1:20 ratio). The data demonstrates $R_1$ values ranging from 0 to approximately 10 $\mu s^{-1}$ and shows linear relationships between $R_1$ and $pO_2$ for each probe composition. The figure illustrates higher oxygen sensitivity compared to LiNc-BuO-LS variants shown in FIG. 4A.

FIG. 5B shows $R_2$ ($=1/T_2$) relaxation rate versus oxygen concentration ($pO_2$) and illustrates parallel data for the same four probe compositions, that is LiNc-BuO-HS, LiNc-BuO-HS+PDMS, LiNc-BuO-HS+BW (1:5), and LiNc-BuO-HS+BW (1:20). The data demonstrates $R_2$ values ranging from 0 to approximately 2 $\mu s^{-1}$ and shows linear relationships between $R_2$ and $pO_2$ for each composition. The figure illustrates how different compositions affect the probe's sensitivity to oxygen and shows an expanded measurement range for composite materials compared to standard LiNc-BuO-HS.

Both FIGS. 5A and 5B demonstrate how embedding LiNc-BuO-HS in different ratios of bonewax modifies the probe's oxygen sensitivity characteristics while maintaining the higher baseline sensitivity of the HS variant compared to the LS variant.

Table 5 (below) states the slope for $R_1$ and $R_2$ with $pO_2$ linear fit for LiNc-BuO-HS, LiNc-BuO-HS-PDMS, LiNc-BuO-HS-BW5, LiNc-BuO-HS-BW20. The change in $R_1$ oxygen sensitivity of these materials compared to LiNc-BuO-HS alone is LiNc-BuO-HS: 1, LiNc-BuO-HS-PDMS: 0.83, LiNc-BuO-HS-BW5: 1, LiNc-BuO-HS-BW20: 0.83. The change in $R_2$ oxygen sensitivity of these materials compared to LiNc-BuO-HS alone is LiNc-BuO-HS: 1, LiNc-BuO-HS-PDMS: 0.86, LiNc-BuO-HS-BW5: 1.63, LiNc-BuO-HS-BW20: 1.63.

TABLE 5

| Probe | $R_1$ or $1/T_1$(Slope) | $R_2$ or $1/T_2$ (Slope) |
|---|---|---|
| LiNc-BuO-HS | 6 | 8 |
| LiNc-BuO-HS-PDMS | 5 | 7 |
| LiNc-BuO-HS-BW5 | 6 | 13 |
| LiNc-BuO-HS-BW20 | 5 | 13 |

FIG. 6A-6E illustrates an in vivo application demonstration of the composite probe through multiple panels. Here, an example is shown of using composite probes for obtaining $pO_2$ in the probes, when the animal breathes 21% $O_2$ and 100% $O_2$ and the $pO_2$ maps can be acquired in these conditions. Note that using unmodified LiPc, the measurement above 5% $O_2$ is not possible using pEPR due to the very short relaxation times of the unaltered probe approaching to the instrument deadtime.

Figure 6A:
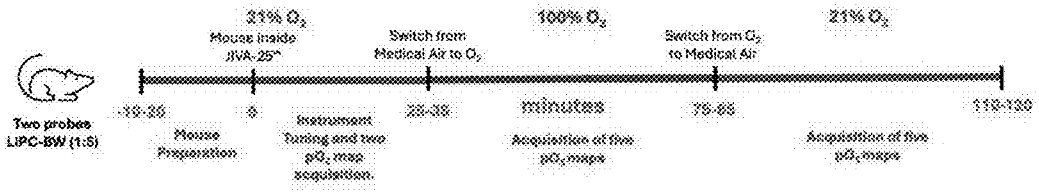
FIG. 6A illustrates a timeline, according to one example.

For example, FIG. 6A shows the experimental timeline with distinct phases including:

Initial 21% $O_2$ phase with mouse preparation (~10-20 minutes)

Instrument tuning and baseline $pO_2$ map acquisition at 21% $O_2$ breathing (0-25 minutes)

100% $O_2$ breathing phase with five $pO_2$ map acquisitions (25-75 minutes)

Return to 21% $O_2$ with five additional $pO_2$ map acquisitions (75-120 minutes)

Figure 6B:
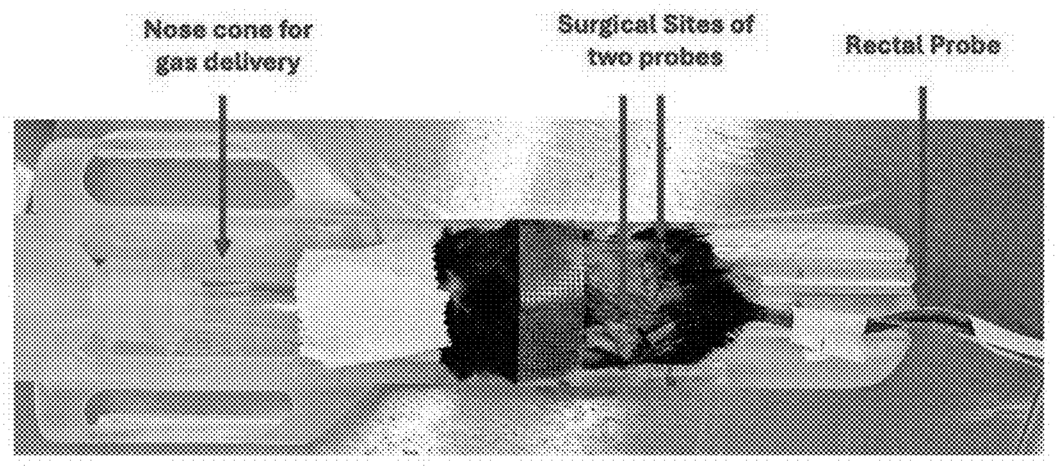
FIG. 6B illustrates mouse preparation, according to one example.

FIG. 6B displays the experimental setup showing a mouse positioned on the imaging cradle, a nose cone for gas delivery, surgical sites where two LiPc-BW5 probes were implanted, and a rectal probe placement for monitoring.

FIG. 6C shows the animal with the probes implanted in the subcutaneous region.

FIG. 6D depicts a single LiPc-BW5 probe with dimensions including length of approximately 10 mm and width of approximately 2.5 mm.

Figure 6E:
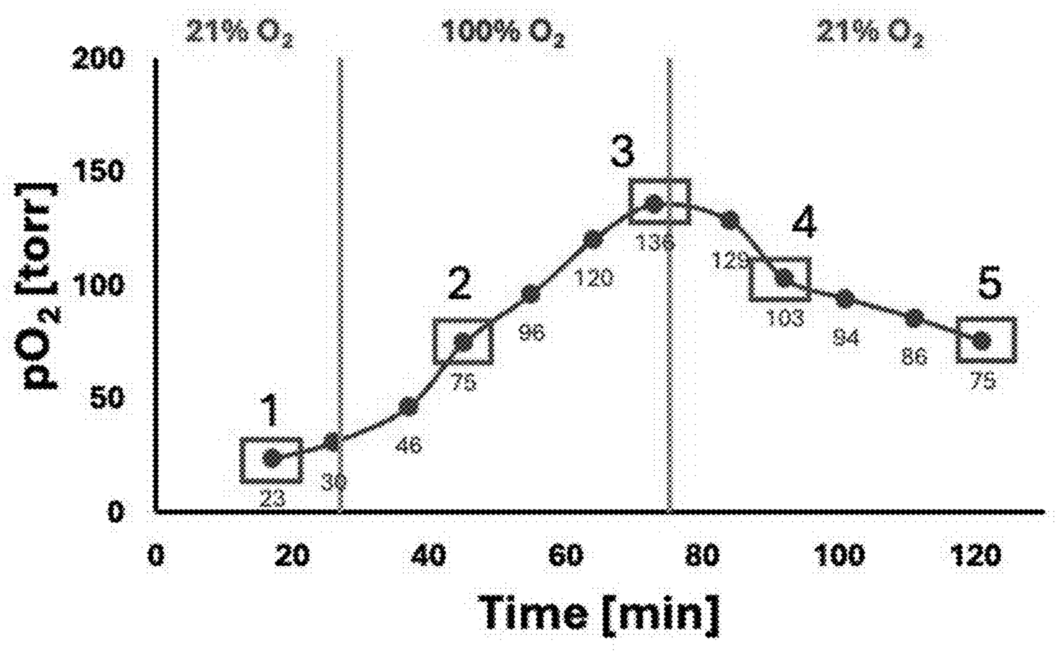
FIG. 6E illustrates $pO_2$ measurements over time, according to one example.
Figure 6F:
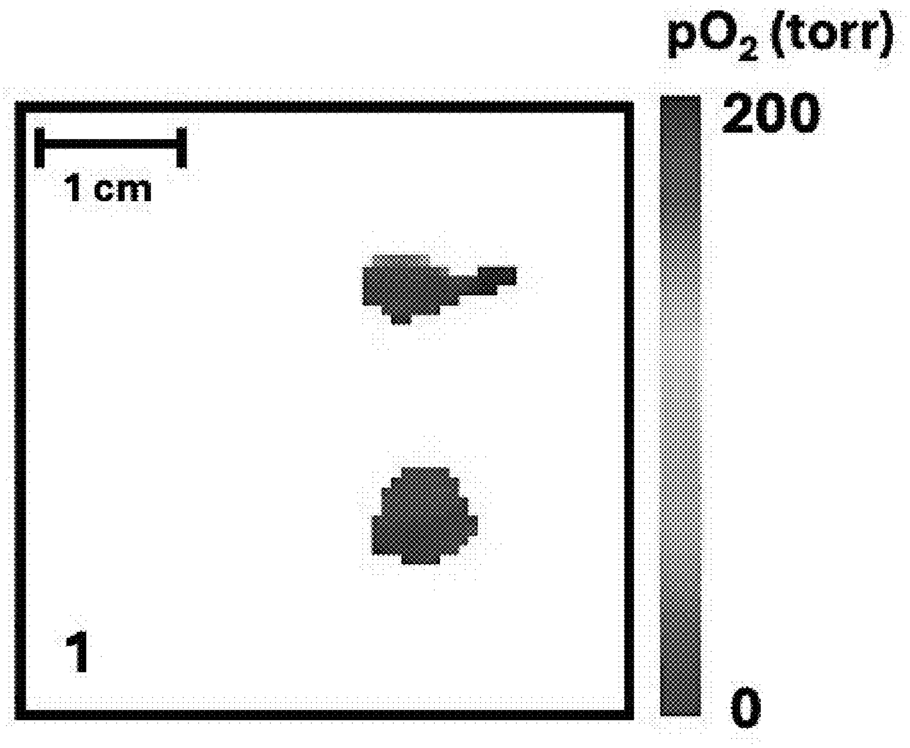
FIGS. 6F-6J illustrate $pO_2$ maps at selected timepoints, according to one example.
Figure 6G:
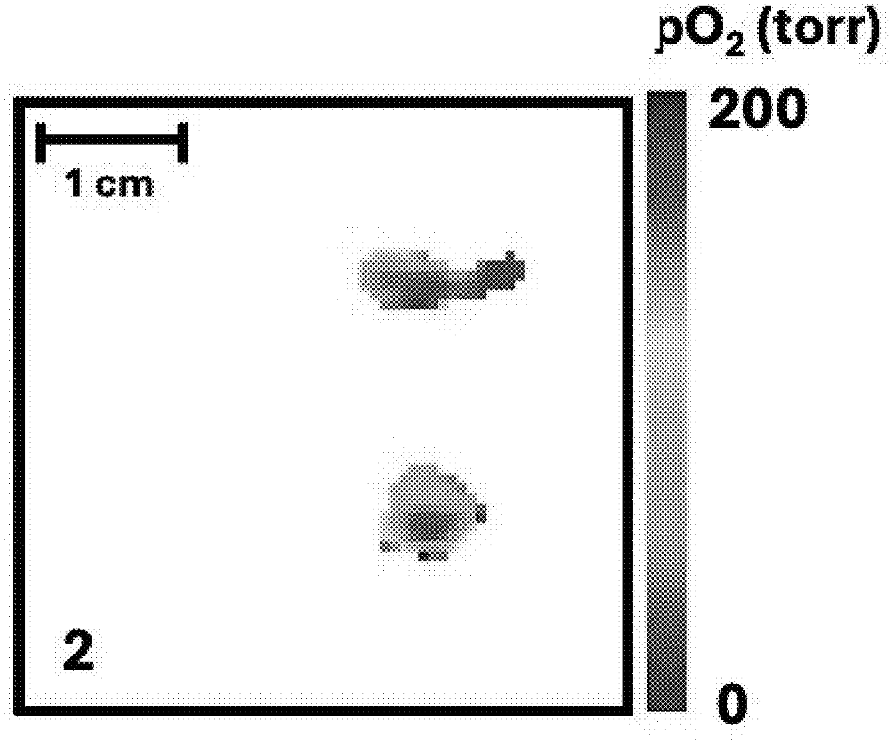
Figure 6H:
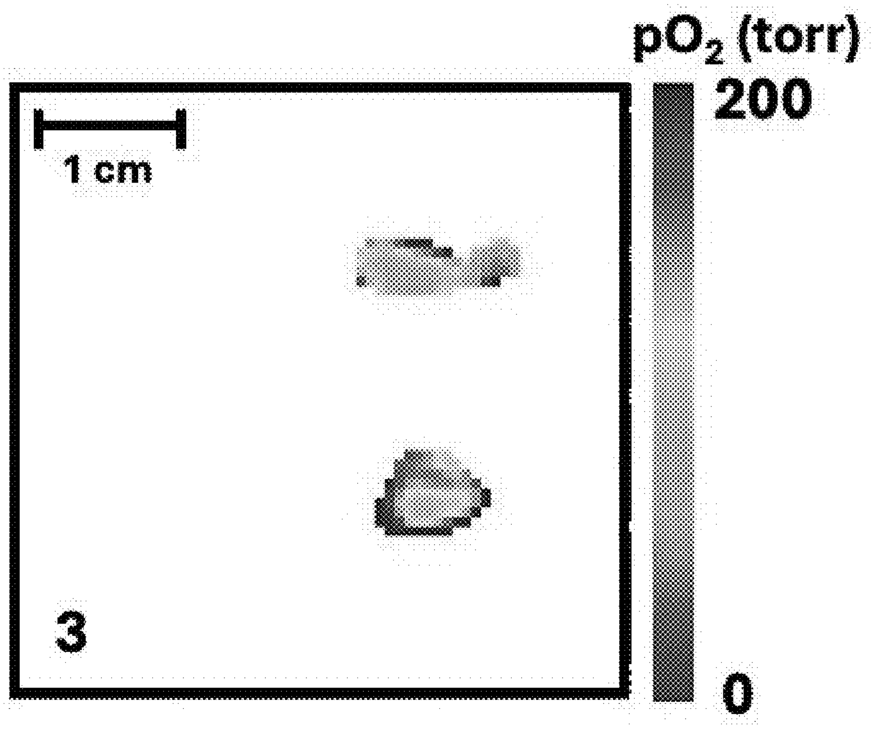
Figure 6I:
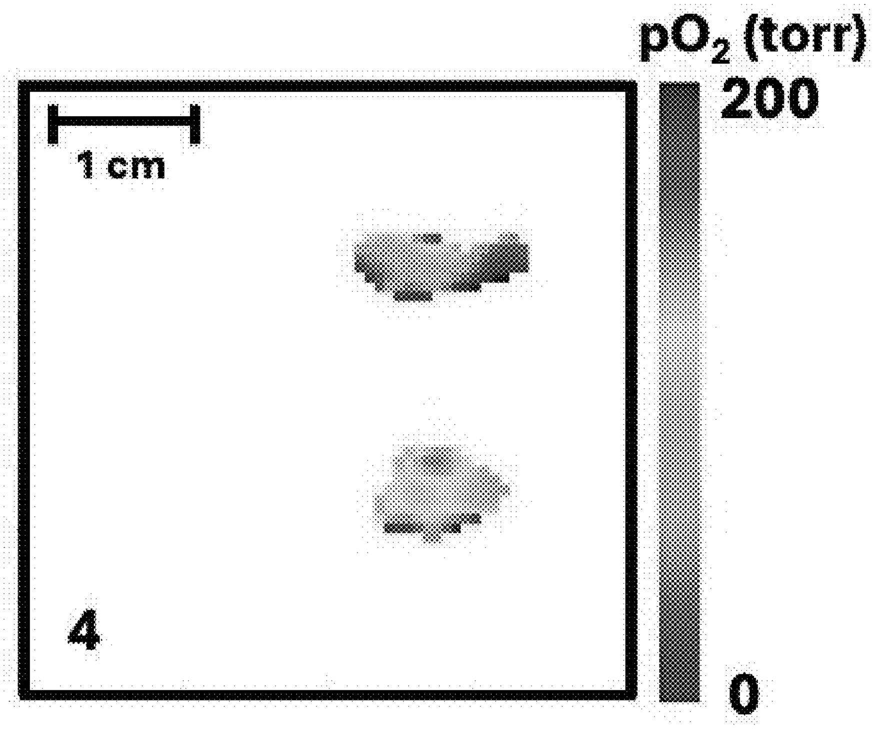
Figure 6J:
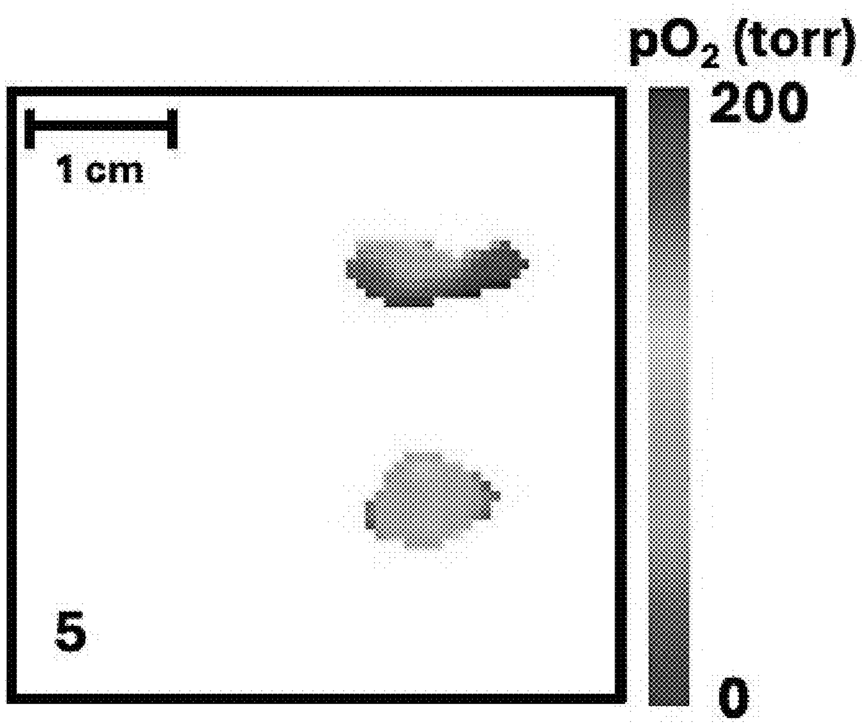

FIG. 6E displays the $pO_2$ values over time during the experiment. The figure shows the initial baseline at 21% $O_2$, elevation during 100% $O_2$ breathing, return to baseline during final 21% $O_2$ phase, and values ranging from approximately 23 to 150 torr.

FIGS. 6F, 6G, 6H, 6I, and 6J show $pO_2$ maps at each of five selected time points during the experiment, demonstrating the spatial distribution of oxygen measurements and the probe's response to changing oxygen conditions.

Figure 7A:
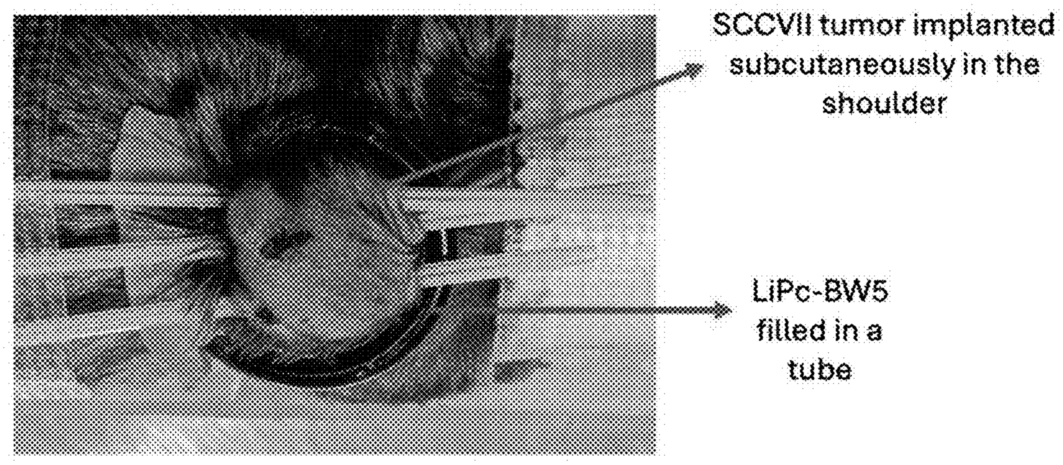
FIG. 7A illustrates a composite probe relative to selected tissue, according to one example.
Figure 7B:
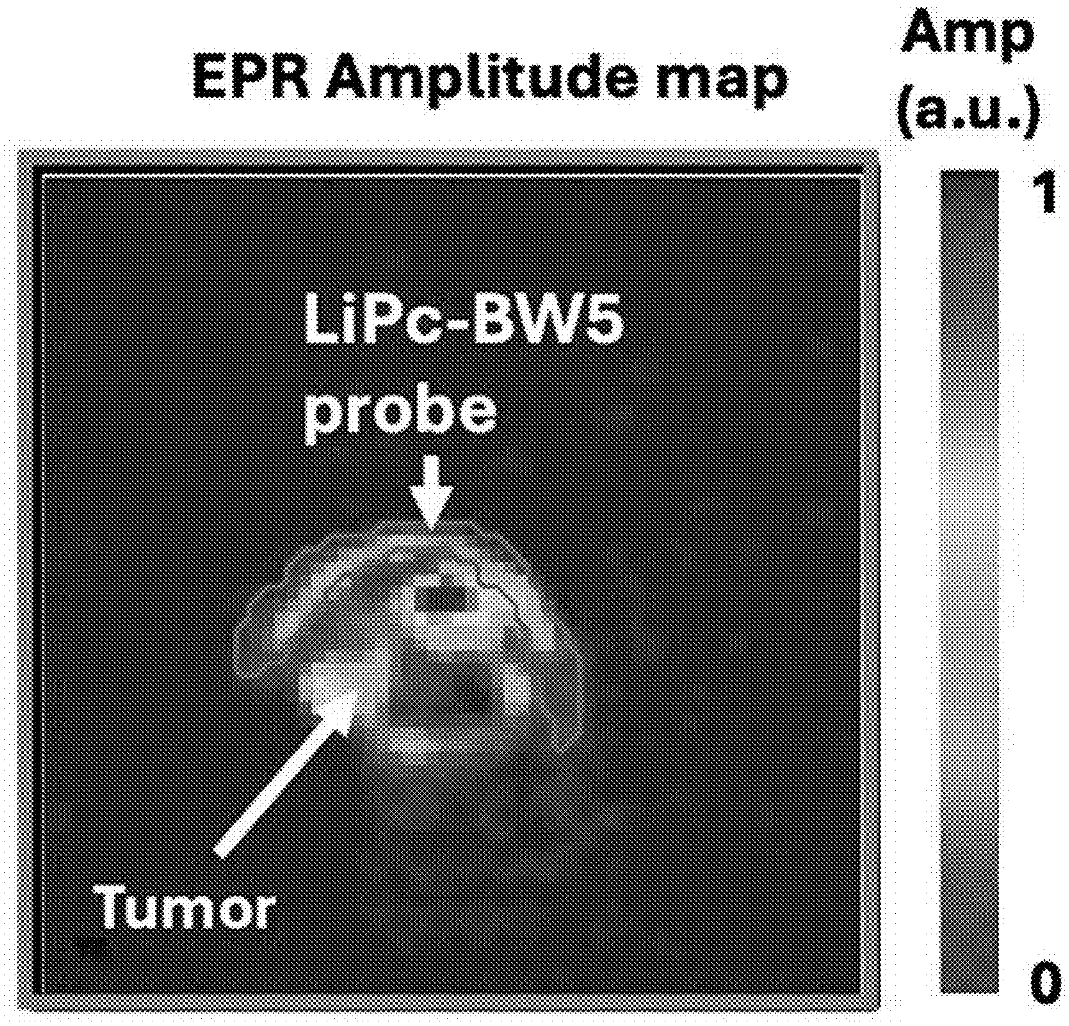
FIG. 7B illustrates an EPR amplitude map, according to one example.
Figure 7C:
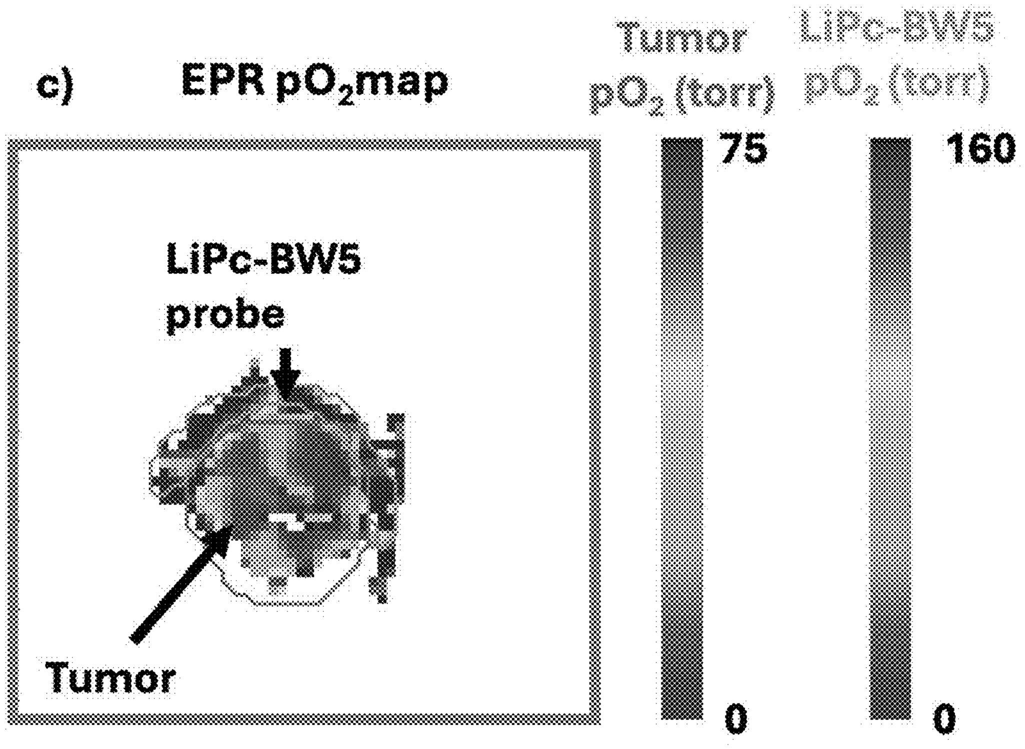
FIG. 7C illustrates a $pO_2$ map, according to one example.

FIGS. 7A-7C demonstrate the application of the composite probe as a tumor marker through three distinct panels. For example, FIG. 7A shows the experimental setup. In the figure, a squamous cell carcinoma (SCC7) tumor is implanted subcutaneously in the shoulder region. A tube filled with LiPc-BW5 composite probe is arranged in a circle around the tumor. The strategic placement is configured to enable tumor location identification in EPR images and co-register with other modalities by modifying the composite probe to add modality-specific material.

FIG. 7B presents the EPR amplitude map. The figure shows that the composite probe is visible and highlighted in magenta to indicate its location. The figure shows clear contrast between the probe signal and the surrounding tissue. In this example, the probe forms a continuous ring-like image around the tumor region.

FIG. 7C displays the EPR $pO_2$ map of tumor and of the composite probe marker. In this case the market is LiPc-BW5. The map illustrates a central region showing tumor $pO_2$ measurements acquired using a soluble EPR probe (trityl OXO1). The figure depicts a boundary region showing $pO_2$ maps of the LiPc-BW5 composite probe. The figure depicts the integration of both measurement types to provide comprehensive tumor location and oxygenation information. In this example, the $pO_2$ values range from 0 to 75 torr on the scale for the tumor and from 0 to 160 torr on the scale for the LiPc-BW5 marker. It illustrates that the composite probe serves as an effective fiducial marker for tumor localization.

The marker can be further modified by adding materials that are visible in other imaging modalities. f.e., if we add water, it will become visible in magnetic resonance imaging, making it a suitable marker for image registration between MRI and EPRI. Similarly, the marker will be visible directly in computed tomography (CT) images due to solid particles or can be modified with barium salts for getting better contrast in CT images and can be used for image registration between CT and EPRI. It can be modified with radioisotopes to make it visible in Positron Emission Tomography (PET) images and registration between PET and EPRI. Any combination of these materials can be used for multi-modality image registration. This makes the composite probe a suitable marker for image registration between modalities.

VARIOUS NOTES

The above description includes references to the accompanying drawings, which form a part of the detailed description. The drawings show, by way of illustration, specific embodiments in which the invention can be practiced. These embodiments are also referred to herein as "examples." Such examples can include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Geometric terms, such as "parallel", "perpendicular", "round", or "square", are not intended to require absolute mathematical precision, unless the context indicates otherwise. Instead, such geometric terms allow for variations due to manufacturing or equivalent functions. For example, if an element is described as "round" or "generally round," a component that is not precisely circular (e.g., one that is slightly oblong or is a many-sided polygon) is still encompassed by this description.

The above description is intended to be illustrative, and not restrictive. For example, the above-described examples (or one or more aspects thereof) may be used in combination with each other. Other embodiments can be used, such as by one of ordinary skill in the art upon reviewing the above description. The Abstract is provided to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

The invention claimed is:

1. A composite probe for electron paramagnetic resonance comprising:
- a particulate or crystalline paramagnetic probe; and
- a non-paramagnetic additive material mixed with the paramagnetic probe;
- wherein the non-paramagnetic additive material modifies the sensitivity of the probe's relaxation rate constants and sensitivity to oxygen partial pressure.

2. A method of manufacturing a composite probe for electron paramagnetic resonance comprising:
- providing a particulate or crystalline paramagnetic probe;
- providing a non-paramagnetic additive material;
- heating the non-paramagnetic additive material;
- mixing the heated non-paramagnetic additive material with the particulate paramagnetic probe to form a composite mixture; and
- shaping the composite mixture into a selected form.

3. A method of using a composite probe for electron paramagnetic resonance measurements comprising:
- implanting a composite probe including a particulate paramagnetic material mixed with a non-paramagnetic additive material into tissue;
- subjecting the implanted composite probe to electron paramagnetic resonance measurements; and
- determining oxygen partial pressure in the tissue based on the electron paramagnetic resonance measurements.

4. The composite probe of claim 1, wherein the particulate paramagnetic probe includes lithium phthalocyanine (LiPc) or lithium octa-n-butoxynaphthalocyanine (LiNc-BuO).

5. The composite probe of claim 1, wherein the non-paramagnetic additive material includes a waxy substance or petroleum-derived oily hydrocarbons.

6. The composite probe of claim 1, wherein the non-paramagnetic additive material is bonewax, beeswax, or petroleum jelly.

7. The composite probe of claim 1, wherein the particulate paramagnetic probe and the non-paramagnetic additive material are mixed in a ratio between 1:5 and 1:20.

8. The composite probe of claim 1, wherein a weight of the particulate paramagnetic probe is at least 10 mg and a weight of non-paramagnetic additive material is at least 50 mg.

9. The composite probe of claim 1, wherein the composite probe exhibits reduced oxygen sensitivity and expanded dynamic range for EPR oximetry compared to the particulate paramagnetic probe alone.

10. The composite probe of claim 1, wherein the composite probe is capable of measuring oxygen concentrations in a range of 0 to 760 torr.

11. The composite probe of claim 1, wherein the composite probe has a conformable shape suited for tissue implantation.

12. The composite probe of claim 1, wherein the composite probe has a tubular configuration.

13. The composite probe of claim 1, wherein the composite probe is configured as a fiducial marker visible in both EPR imaging and at least one other imaging modality selected from computed tomography, magnetic resonance imaging, and ultrasound imaging.

14. The composite probe of claim 1, wherein the composite probe includes a barium salt.

15. The composite probe of claim 1, wherein the composite probe includes water.

16. The method of claim 2, wherein:
- the particulate paramagnetic probe includes lithium phthalocyanine (LiPc); and
- the non-paramagnetic additive material includes bonewax; and
- wherein the mixing includes combining 10 mg of LiPc with 50 mg of bonewax.

17. The method of claim 2, wherein heating the non-paramagnetic additive material comprises:
- placing the non-paramagnetic additive material in a petri dish;
- heating the non-paramagnetic additive material to 37° C.-60° C.
- mashing the material using a steel rod; and
- heating the material in a microwave for approximately one minute.

18. The method of claim 2, wherein providing the non-paramagnetic additive material includes selecting at least one of bonewax, beeswax, and petroleum jelly.

19. The method of claim 2, wherein mixing includes combining the particulate paramagnetic probe and the non-paramagnetic additive material in a ratio between 1:5 and 1:20.

20. The method of claim 2, wherein shaping the composite mixture includes kneading.

21. The method of claim 2, further including encapsulating the shaped composite mixture in plastic.

22. The method of claim 3, wherein determining oxygen partial pressure comprises:
- measuring a relaxation rate of the composite probe; and
- calculating oxygen partial pressure based on a linear relationship between the relaxation rate and oxygen concentration.

23. The method of claim 3, wherein the electron paramagnetic resonance measurements include:
- pulse electron paramagnetic resonance measurements; and
- measuring oxygen concentrations in a range of 0 to 760 torr.

24. The method of claim 3, further comprising:
- monitoring changes in tissue oxygenation during administration of breathing gases; and
- determining oxygen partial pressure as a function of time.

25. The method of claim 3, wherein the composite probe is used as a fiducial marker, the method further comprising:

arranging the composite probe near a region of interest; and using the composite probe to locate the region of interest in electron paramagnetic resonance images.

26. The method of claim 3, further comprising:

using the composite probe as a marker visible in at least one imaging modality selected from computed tomography, magnetic resonance imaging, and ultrasound imaging.

27. The method of claim 3, wherein:

the particulate paramagnetic material includes lithium phthalocyanine (LiPc) or lithium octa-n-butoxynaphthalocyanine (LiNc-BuO); and the non-paramagnetic additive material includes bone-wax, beeswax, or petroleum jelly.

28. The method of claim 3, wherein the composite probe exhibits reduced oxygen sensitivity and expanded dynamic range compared to the particulate paramagnetic probe alone, enabling pulse electron paramagnetic resonance measurements at elevated oxygen levels.

29. The composite probe of claim 1, wherein the composite probe includes a radioisotope for positron emission tomography.

* * * * *